United States Patent [19]

Tarin et al.

[11] Patent Number: 5,830,646

[45] Date of Patent: Nov. 3, 1998

[54] DIAGNOSTIC METHOD

[75] Inventors: David Tarin, Oxford, United Kingdom; Yasuhiro Matsumura, Tokyo, Japan

[73] Assignee: Isis Innovation Limited, Oxford, United Kingdom

[21] Appl. No.: 373,284

[22] PCT Filed: Jul. 20, 1993

[86] PCT No.: PCT/GB93/01520

§ 371 Date: Apr. 7, 1995

§ 102(e) Date: Apr. 7, 1995

[87] PCT Pub. No.: WO94/02633

PCT Pub. Date: Feb. 3, 1994

[30] Foreign Application Priority Data

Jul. 21, 1992 [GB] United Kingdom .................. 9215498
Nov. 20, 1992 [GB] United Kingdom .................. 9224386
Dec. 16, 1992 [GB] United Kingdom .................. 9226165

[51] Int. Cl.⁶ ............................. C12Q 1/68; C07H 21/04; G01N 33/483
[52] U.S. Cl. ................................ 435/6; 436/64; 536/23.1; 536/24.1; 536/24.31; 536/24.33
[58] Field of Search .................................. 435/6; 436/64; 536/23.1, 23.5, 24.1, 24.3, 24.31, 24.33; 935/77, 78

[56] References Cited

U.S. PATENT DOCUMENTS 5,506,119 4/1996 Herrlich et al. ..................... 435/69.3

OTHER PUBLICATIONS

G.R. Screaton et al. "Genomic structure of DNA . . . " Chemical Abstracts #184829m. vol 118, No. 19 May 10, 1993 (Columbus, Ohio USA), p. 253.

D.L. Cooper et al. "The complex CD44 transcriptional . . . " Chemical Abstracts #122543e vol 118 No. 13, Mar. 29, 1993 (Columbus, Ohio USA), p. 619.

M. Hoffman et al. "CD44 splice variantes . . . " Chemical Abstracts #206116k, vol 117 No. 21, Nov. 23, 1992 (Columbus, Ohio USA), p. 203.

H.J. Harn et al. "The multi–specific cell adhesion . . . " Chemical Abstracts #229300j, vol 116 No. 23, Jun. 8, 1992 (Columbus, Ohio USA), p. 202.

Jackson et al. J. Biol. Chem 26(7) 4732–4739 1992 "Multiple Variants of the Human Lymphocyte Homing Receptor CD44 . . . ".

Günthet et al. Cell 65 13–24 1991 "A New Variant of Glycoprotein CD44 Confers Metastatic Potential to Rat Carcinoma Cells".

Janabe et al. Lancet 341 725–726 1993 "Expression of CD44R1 Adhesion Molecule in Colon Carcinomer & Metastases".

Screcton et al Proc Natl Acad Sci: 89(24) 1992 "Genomic Structure of DNA Encoding the Lymphocyte Homing Receptor CD44 . . . ".

*Primary Examiner*—Nancy Degen
*Attorney, Agent, or Firm*—Nixon & Vanderhye PC

[57] ABSTRACT

There is marked over-expression of multiple spliced variants of the CD44 gene in tumor compared to counterpart normal tissue. This observation forms the basis of a method of diagnosing neoplasia by analysis of a sample of body tissue or body fluid or waste product. A new exon 6 of 129 bp has been located and sequenced, and is claimed as such and for use in a diagnostic method.

9 Claims, 6 Drawing Sheets

STANDARD | New Exon (Exon6)

GCTACCACTTTGATGAGCACTAGTGCTACA
　T　L　M　S　T　S　A　T

GCAACTGAGACAGCAACCAAGAGGCAAGAA
　A　T　E　T　A　T　K　R　Q　E

ACCTGGGATTGGTTTTCATGGTTGTTTCTA
　T　W　D　W　F　S　W　L　F　L

CCATCAGAGTCAAAGAATCATCTTCACACA
　P　S　E　S　K　N　H　L　H　I

ACAACACAAATGGCTGGTACG　　(SEQ ID No:1)
　T　T　Q　M　A | Exon 7

FIG. 7

DIAGNOSTIC METHOD

BACKGROUND

The present invention is concerned with using expression of the CD44 gene or part of the CD44 gene to investigate neoplasia. Such investigation includes taking a tissue, body fluid or other sample from a patient to perform diagnosis, to give a prognosis or to evaluate therapy that is already being carried out. In particular, the invention provides a simple method for carrying out routine screening for neoplasia using body fluid samples or other samples which can be obtained non-invasively.

The usual way to diagnose a tumour at present is by looking at cells or thin slices of tissue down a microscope, a method which is often very effective but has some important limitations. With a small sample, diagnosis can be very difficult and often a large number of cells will not be available, or it is not desirable or possible to obtain a large sample from the patient. In as many as 50% of cases a reliable diagnosis cannot be given; it may be that there is no positive evidence of carcinoma but also no certainty that the patient is actually free from carcinoma. More invasive investigation is then required to establish a diagnosis.

Judgment of prognosis also relies on the appearance of cells when viewed under a microscope. Generally, the more bizarre-looking the cells in a primary tumour, the more likely they are to metastasise later on but the correlation is by no means absolute. It would clearly be an advantage to be able to predict more accurately whether or not metastasis is likely to occur in order to judge what will be the most effective treatment.

The human CD44 gene codes for a family of variably glycosylated cell surface proteins of different sizes, the numerous functions of which are not yet fully established, but which share epitopes recognised by the CD44 monoclonal antibody (mAb). It is known to consist of a standard portion which is expressed in haemopoietic cells and many other cell types and into which the products of additional exons may be spliced in various combinations to produce different proteins. This is a well recognised mechanism in eukaryotes for producing several often functionally unrelated proteins from the same gene, and is known as alternative splicing.

Two common CD44 isoforms have so far been purified and characterised (Stamenkovic et al. 1989), namely i) a 90 kD form consisting of a central 37 kD core which is heavily glycosylated and ii) a 180 kD form which has 135 extra amino acids inserted into the proximal extra-membrane domain and is even more heavily glycosylated. Immunocytochemical and immuno-precipitation studies have shown that both are widely distributed in many different cells and tissues. The former is known as the haemopoietic or standard form which is present on circulating leukocytes, bone marrow cells and numerous other cell types. The other, known as the epithelial variant, is detectable on several epithelial cell types. Both are believed to function as receptors mediating homotypic and heterotypic adhesive interactions, attaching cells to each other or to adjacent extracellular scaffolding.

Some time ago, some of the CD44 epitopes recognised by the mAb Hermes-3 were identified as constituting the peripheral lymph node receptor enabling circulating lymphocytes to recognise and traffic through peripheral lymph nodes. Further mAbs to this antigen later became available and Stamenkovic et al. (1989) used one of them to clone a cDNA sequence coding for the standard form of the molecule from an expression library in COS cells. They additionally found, by Northern blotting, that this gene was expressed not only by lymphoid cells, but also by a variety of carcinoma cell lines and a representative sample of solid carcinomas, amongst which two colonic carcinomas appeared to express more than normal colonic epithelium.

Birch and colleagues (1991) reported that melanoma cell clones which strongly expressed the 80–90 kD form of the CD44 antigen, recognised by the Hermes-3 antibody, were substantially more metastatic in nude mice than clones which expressed it weakly. Sy et al. (1991) described a moderate increase in metastatic capability of human lymphoma cells in nude mice, after the cells were transfected with the standard CD44 gene, but not after transfection with a construct coding for the epithelial variant. Gunthert et al. (1991) obtained results indicating that a variant form of the lymphocyte homing receptor, recognised by a new antibody raised to the rat CD44 antigen, is required for metastatic behaviour of rat pancreatic adenocarcinoma cells. Using this antibody they cloned a cDNA sequence corresponding to the variant form of CD44 and found that it contained previously unidentified exons. Transfection of a non-metastatic clone from the same cell line with a construct designed to over-express this cDNA sequence unique to the metastatic counterpart, appeared to induce metastatic behaviour (Gunthert et al, 1991).

In view of these findings it became of interest to know whether other cultured metastatic and non-metastatic human tumour cell lines, of various histogenetic origins, expressed CD44 products differentially. The expression of genes in cells or tissues can be studied most efficiently and sensitively by making cDNA from cellular messenger RNA and amplifying regions of interest with the polymerase chain reaction, using specific oligonucleotide primers chosen to anneal preferentially to portions of the cDNA corresponding to the gene products. However, subsequent work by Hofmann et al. (1991) and the present applicants using this approach provided results which showed that CD44 expression did not regularly and reliably correlate with the metastatic capability or even tumour forming ability of these cultured cell lines in nude mice. At about this time, three separate groups (Hofmann et al, 1991, Stamenkovic et al, 1991 and Jackson et al, 1992) published sequence data on further splice variants they had found being expressed by this gene in various human cell lines.

THE INVENTION

The present invention results from a surprising discovery resulting from studies examining the expression of various parts of the CD44 gene in fresh tissue and body fluid samples from patients with tumours of the breast and colon and from their metastases. The results indicate sharp and clear differences in CD44 expression between tissues from i) metastatic (malignant) tumours, ii) non-metastatic locally invasive tumours and benign tumours and iii) normal tissue. The distinction between groups i) and ii) is important for judgment of therapy and that between groups ii) and iii) is important for early diagnosis and screening.

The invention therefore provides in one aspect a method of diagnosis of neoplasia, which method comprises analysing the expression of the CD44 gene in a sample.

In a particular embodiment, the invention provides a method of assaying a sample for products of the CD44 gene or part thereof which method comprises making cDNA from messenger RNA (mRNA) in the sample, amplifying portions of the complementary DNA (cDNA) corresponding to the CD44 gene or part thereof and detecting the amplified cDNA, characterised in that the amplified cDNA is used in diagnosis of neoplasia.

The diagnosis of neoplasia may refer to the initial detection of neoplastic tissue or it may be the step of distinguishing between metastatic and non-metastatic tumours. References to the term "diagnosis" as used herein are to be understood accordingly.

The method is particularly applicable to the diagnosis of solid tumours particularly malignant tumours e.g. carcinomas. The sample on which the assay is performed is preferably of body tissue or body fluid; and not of cells cultured in vitro. The sample may be a small piece of tissue or a fine needle aspirate (FNA) of cells from a solid tumour. Alternatively, it may be a sample of blood or urine or another body fluid, a cervical scraping or a non-invasively obtained sample such as sputum, urine or stool.

The cDNA may be detected by use of one or more labelled specific oligonucleotide probes, the probes being chosen so as to be capable of annealing to part of the amplified cDNA sequence. Alternatively, labelled oligonucleotide primers and/or labelled mononucleotides could be used. There are a number of suitable detectable labels which can be employed, including radiolabels.

BRIEF DESCRIPTION OF THE DRAWINGS

Reference is directed to the accompanying drawings, in which:

FIG. 7 is the nucleic acid sequence of Exon 6 (shown in FIG. 6) (SEQ ID NO:1), the corresponding amino acid sequence being also shown (SEQ ID NO:2)

FIG. 6 is a map of the CD44 gene showing exons 6 to 14. The basic or standard protein can theoretically be modified by the insertion of transcripts from any, some, or all of these 9 extra exons. Exon 6 was unknown at the priority date of this patent application, and constitutes a further aspect of the invention. Exon 6 is over-expressed in tumours but not in normal tissues, and is located in the vicinity of exons 7 to 9. The sequence of exon 6 is given in FIG. 7. It contains 129 base pairs and is flanked on the 5'-side by the standard CD44 sequence, and on the 3'-side usually by exon 7.

Figure 1A:
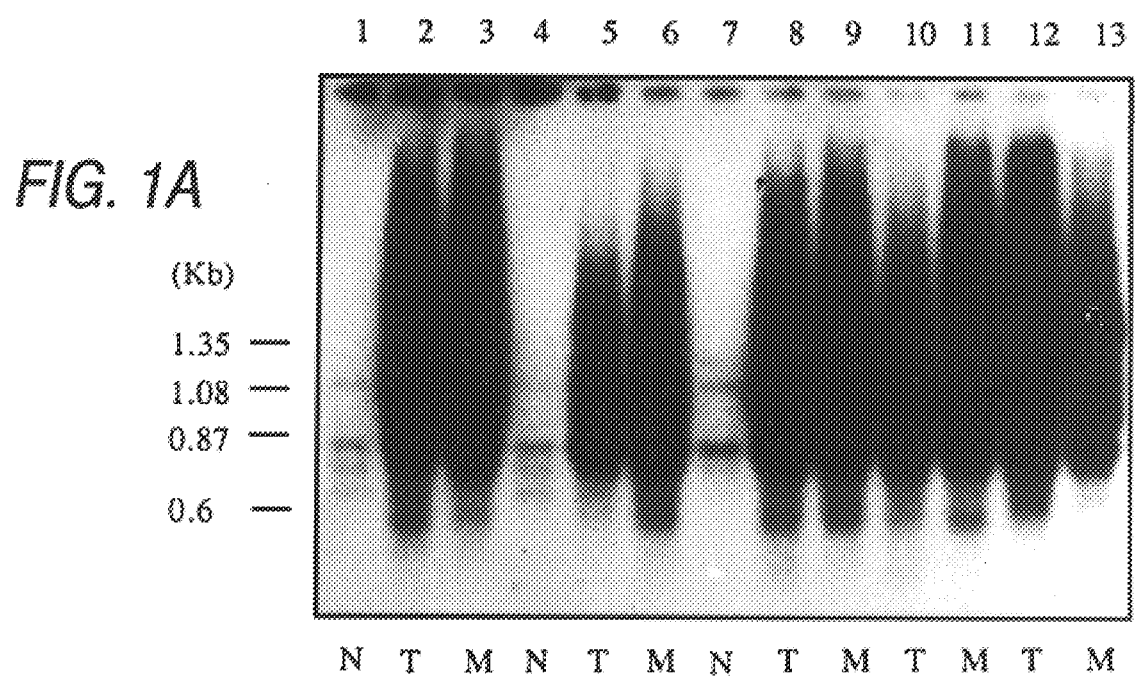
FIGS. 1A, 1B, 1C, 2A, 2B, 2C, 3, 4, 5A, and 5B are autoradiographs showing the results of various experiments reported below.

In contrast to Exons 9 to 11, the products of Exon 6 (the newly-sequenced Exon) are only barely detectable in samples of normal tissues. This suggests that Exon 6 will be of particular value in the diagnosis of neoplasia.

In another aspect, this invention provides as new compounds, the nucleic acid sequence of Exon 6 as shown in FIG. 7, characteristic fragments thereof, sequences which are degenerated and/or represent allele variations, the homologous nucleic acid sequences, and probes, primers and other reagents capable of hybridising with the sequences or homologues. These compounds and reagents will all be useful in the method described above.

Further aspects of this invention include:

The peptide sequence, corresponding to Exon 6 and shown in FIG. 7, its allele variations and secondary modifications thereof, like phosphorylation and glycosylation products, and characteristic fragments thereof, for example those fragments which constitute epitopes when the polypeptide is folded in vivo.

Antibodies to the peptide sequence, its allele variations and secondary modifications thereof, like phosphorylation and glycosylation products and the characteristic fragments thereof. Such antibodies may be labelled, for example with a radionuclide or with a tumouricidal compound.

Use of a labelled antibody for in vitro diagnosis.

Use of such a radiolabelled antibody for radioimaging or in vivo diagnosis.

Use of the antibodies, optionally labelled with tumouricidal compounds or otherwise, in therapy.

The peptide sequence or fragment can be synthesised by standard techniques, e.g. using an automatic synthesiser. The antibodies can be made by administering the peptide in antigenic form to a suitable host. Polyclonal or monoclonal antibodies may be prepared by standard techniques.

In a further aspect, the invention provides a method for the immunological diagnosis of neoplasia, characterised by determining over-expression of an exon located in the vicinity of exons 7 to 9 of the CD44 gene. Preferably the exon has the nucleic acid sequence shown in FIG. 7.

The chaotic over-expression of multiple spliced variants of the CD44 gene in tumours, implies that a particular exon may or may not be over-expressed (or expressed at all) by a particular tissue sample. An immunoassay using an antibody to the peptide expressed by any single exon may therefore give misleading results. This invention therefore includes use, for the immunological diagnosis of neoplasia, of a mixture of antibodies to two or more, and preferably to all nine, of the CD44 exons.

DETAILED DESCRIPTION

In one embodiment of the invention, the amplification of cDNA is carried out using the polymerase chain reaction (PCR). For PCR, primers may be chosen using known sequence information for human CD44 cDNA. Primers may be used that amplify cDNA corresponding to any part of the CD44 gene that may be expressed. This may include the standard portion with or without the inserted exons, or it may be part or all of one or more of the exons only. In the latter case there would be less wastage of reagents and a better signal produced, and a probe for the standard sequence would not be used.

The invention is not limited to the use of straightforward PCR. A system of nested primers may be used for example. Other suitable amplification methods known in the field can also be applied.

In another method according to the invention, the amplified cDNA is separated by electrophoresis. Blotting and autoradiography may then be performed on the separated cDNA. Autoradiography involves probing electrophoresed amplified products, immobilised by blotting them on to a nylon membrane, with a radiolabelled specific oligonucleotide probe labelled with $^{32}P$ or other suitable label, the probe being chosen so as to be capable of annealing to part of the amplified cDNA sequence. The detection step then involves exposure of the labelled, separated cDNA to X-ray film.

In the examples which follow it was found that expression of the human CD44 gene was consistently and distinctively increased in various solid tumours relative to normal tissues. Malignant (i.e. already metastatic) tumours differed from locally invasive and benign ones in the pattern and magnitude of changes seen. The study was performed on samples from 46 tumours of which 44 were locally invasive, or metastatic and 2 were benign. Analysis of CD44 expression was performed by using PCR to amplify cDNA made by reverse transcription of RNA extracted from fresh surgical biopsy samples. By choosing oligonucleotide primers which specifically anneal to certain portions of the CD44 gene, it is possible to amplify portions of the gene which, from these results, are of diagnostic and prognostic interest.

The strong association found here, between altered CD44 expression and neoplasia, need not imply that any of the individual exons of the gene are expressed only in neoplasia or in progression to metastatic malignancy. Evidence accrued in many laboratories in recent years (see Knudson 1985, Tarin 1992, Hayle et al 1992 for reviews) indicates that these pathological processes are probably the consequences of disturbed regulation of genes coding for normal cellular activities such as cell proliferation and migration. Therefore it seems unlikely that any gene, or portion of a gene, has the sole function of programming neoplasia or metastasis.

The finding in the present study of transcripts from exon 10/11 in normal tissues, indicates that this exon is not exclusively concerned with metastatic activity, even though there is marked increase in the number and signal intensity of bands hybridising with radiolabelled probe E4 in the PCR products from tumours capable of metastasis. Other supporting events are therefore believed to be required for CD44 exon 10/11 expression to result in metastatic behaviour. Nevertheless, the observation that transcripts from this exon were over-expressed in samples from metastatic tumours promises to be a very useful indicator of prognosis.

It is not expected that further research will find that the natural (non-mutated) products of any individual exon will be uniquely present in tumour cells and not in normal counterparts. Instead, it is likely that an abnormal pattern of gene activity consisting of over-expression and inappropriate combination of products of a gene, such as that reported here for the CD44 locus, could play a part in malignancy. These changes may themselves be required for malignant conversion, or be the consequence of other genetic disturbances causing such a conversion. Even so, without resolving this issue, an observer using these techniques can obtain information relevant to assigning a sample to neoplastic or non-neoplastic categories.

EXAMPLES

Method

Fresh tissue samples, 0.5–1 cm diameter, were obtained from surgical resection specimens removed at therapy of 34 patients with breast tumours and colon tumours. The samples were snap-frozen in liquid nitrogen within ten minutes of arrival in the pathological specimen reception area and kept in liquid nitrogen until use. Portions of lymph node metastases and blood-borne metastases were also collected, if present, in the tissue resected for diagnosis. Normal breast tissue, normal colon mucosa, normal lymph node adjacent to the tumour in the breast and normal liver were also collected from the surgically resected samples and from other samples removed for non-neoplastic conditions. Normal peripheral blood leukocytes were obtained from 10 volunteers and bone marrow from 3 volunteers. The histological features of the tumours and their clinical stages were as described in Table 1.

Total cellular RNA extraction from tissue samples was performed according to the method described by Chomizynski and Sacchi (1987). Extraction from fluid samples was by use of the Microfasttrack kit marketed by Invitrogen. cDNA synthesis and subsequent amplification by the polymerase chain reaction (PCR) was performed using the Superscript™ preamplification system (BRL Life Technologies Inc., Middlesex, UK) with buffers and reagents supplied in this kit. In brief, this involves an initial step of first strand cDNA synthesis with reverse transcriptase, using sample RNA as the template and supplied nucleotide triphosphates. For subsequent PCR each sample was overlaid with oil and heated at 94° C. for 5 minutes to denature nucleic acid; 30 cycles of PCR were then conducted with the following cycle parameters: 94° C. for 1 m, 55° C. for 1 m, 72° C. for 2 m. Negative controls in which there was no template cDNA in the reaction mix, were routinely run with each batch. The primers and probe sequences we devised, using information from the published sequence for human CD44 cDNA (Hofmann et al, 1991, Stamenkovic et al, 1991, Jackson et al, 1992) (FIG. 6) were as follows:

P1=5'GACACATATTGCTTCAATGCTTCAGC (SEQ ID NO:3)

P4=5'GATGCCAAGATGATCAGCCATTCTGGAAT (SEQ ID NO:4)

Figure 6:
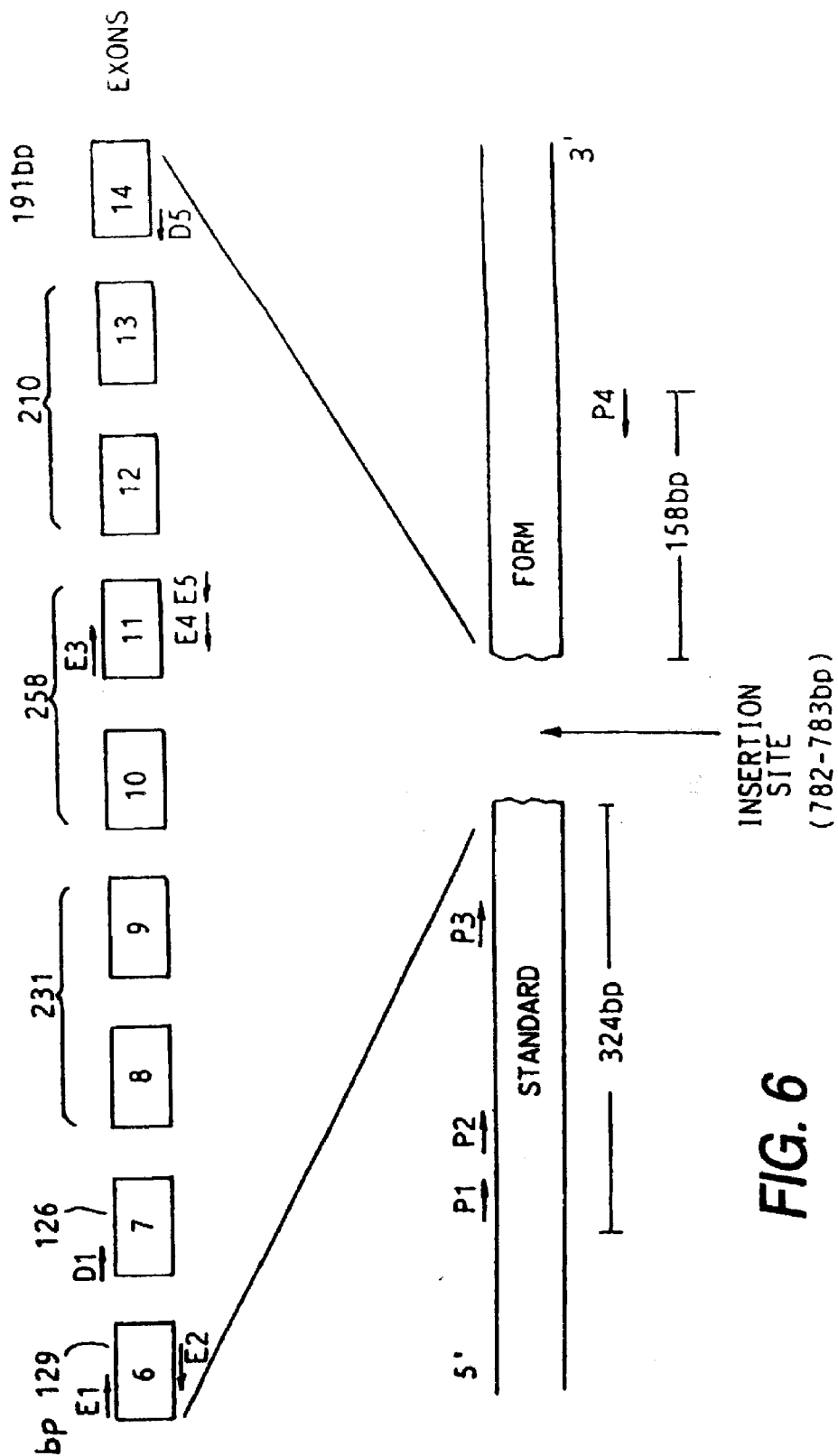
FIG. 6 is a map of the CD44 gene showing exons, probes and primers. The numbering of the exons corresponds to that used by G. R. Screaton et al. 1992)

P1 is located with its origin 324 bp upstream from the insertion site in the standard CD44 molecule (between nucleotides 782 and 783 in the sequence published by Stamenkovic et al, 1989) and P4 is 158 bp downstream of this site. These primers produce a PCR fragment of 482 bp if a sample expresses standard CD44 (so-called haemopoietic CD44), 878 bp for the epithelial form of CD44 and several other bands, if a sample contains alternatively spliced transcripts. 10 μl of each PCR product was electrophoresed in a 1.2% agarose gel and transferred to Hybond N+ (Amersham UK, Little Chalfont, UK) nylon membranes for hybridisation with oligonucleotide probe E4 (=5'TGAGATTGGGTTGAAGAAATC-3'), (SEQ ID NO:5) see FIG. 6. Blotting and autoradiography were performed to improve sensitivity of detection and resolution. The probe was radiolabelled with $y^{32}P$-ATP in the presence of polynucleotide kinase. After prehybridisation, hybridisation was performed in 10% dextran, 6×NET, 5×Denhardt solution, 0.5% NP40 and 100 μg/ml salmon sperm DNA at 42° C. overnight. The filter was then washed twice in 2×SSC, 1×SSC and 0.5% SSC with 0.1% SDS at 42° C. sequentially for 15 minutes each. Filters were exposed to Kodak X-ray film for 2–16 hours. After this, the filters were boiled in 0.5% SDS for stripping the probe and rehybridised with another radiolabelled probe, namely P2 (=5'CCTGAAGAAGATTGTACATCAGTCACAGAC) (SEQ ID NO:6) we designed to anneal to the standard portion of the CD44 (FIG. 6). The conditions used for hybridisation, washing and autoradiography were the same as above.

Calibration of the sensitivity of the method, for detection of small numbers of cells was performed as follows: total peripheral blood leukocytes (PBL) were purified from 20 ml whole blood by lysis of packed red blood cells by addition of ammonium chloride buffer (1 ml packed cells to 50 mls lysis buffer) and subsequent centrifugation 15 minutes later. The white cell pellet was divided into 4 tubes which were seeded respectively with 0 μl, 1 μl, 10 μl and 100 μl of a suspension of HT29 colon carcinoma cells (5000 cells per ml). Total RNA was then extracted and each tube yielded approximately 20 μg. cDNA synthesis was performed, as described above on 4μg aliquots of the RNA obtained from each tube representing 0, 1, 10 and 100 tumour cells per aliquotted sample respectively. The PCR was performed on these samples and on positive (tumour cells only) and negative (no DNA) controls using primers D1 and D5 which were designed by us to anneal specifically to exons 7 and 14 in FIG. 6. We know from previous studies that HT29 cells express both exons, and others, in a pattern easily distinguishable from PBL and chose the oligonupleotide primers D1 and D5 because we wished to increase sensitivity by shortening the segment to be amplified. It was also reasoned that use of these primers would circumvent the problem of using primers P1 and P4 for this specific purpose because the majority of these would be soaked up by annealing to the standard portion of the gene. PCR cycle parameters, blotting, probing and washing conditions were as described above. The oligonucleotide sequence used for probing was $^{32}$P labelled E4.

General Overview of Results

As the primers (P1 and P4) amplify across the splice product insertion site it is clear that the intervening part of the standard molecule will be amplified, in addition to any alternatively spliced variants which contain transcripts from the additional exon domains. Hence the total number of products which could conceivably be detected with a probe (e.g. P2) to the standard form considering all possible combinations of the sequences identified from this locus, is large. Using probe E4, 16 of these combinations, namely those containing E4 transcripts from exon 11, could potentially be visualised as bands of different molecular sizes resolved by electrophoresis. In practice the full range of possible combinations was not detected in these results, but several (up to 9) alternative splice variants were seen in neoplastic tissues hybridised with each probe. Normal tissues from the breast, colon and lymph nodes did express some E4-containing transcripts (FIGS. 1 and 3), in addition to the standard molecule (FIGS. 2 and 4), but peripheral blood leukocytes (FIG. 5) and liver (FIG. 4) detectably expressed only the latter with this combination of probes and primers. The details are presented below:

EXAMPLE 1

Breast Tissue Samples

The results obtained in the study of breast tissue samples are illustrated in FIGS. 1 and 2. Metastatic tumour deposits and their corresponding primary tumours from all cases over-expressed several alternatively spliced products containing transcripts from exon 11 (FIG. 1a). At least 8 separate bands were frequently seen together with a consistent doublet at 1500 bp and 1650 bp present in all tumours. Normal breast tissue and normal lymph node produced two bands (1150 bp and 860 bp) with this probe. The doublet mentioned above was not seen in any normal sample.

The differences between the number, and size of the bands and the intensity of signal from the bound probe, between tissues in normal and malignant categories, was obvious in all samples examined. For occasional samples it was necessary to expose the filter to the X-ray film for longer, to see the distinctive differences, but this finding was confirmed in every case studied.

Figure 1B:
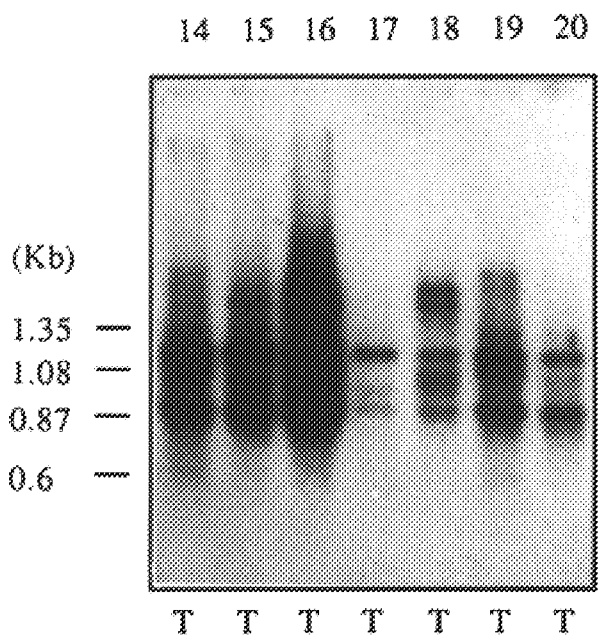

Samples from locally invasive tumours with no associated clinical evidence of metastasis and from the two fibroadenomas also over-expressed splice products containing transcripts from exon 10/11 relative to normal tissues, but the extent of this was easily distinguished from the results obtained with malignant tumours and their metastases. Distinction from the patterns seen in normal tissues was also easy (FIG. 1b). However, a single sample gave a similar result to malignant tumours (lane 14) (see below). The two fibroadenomas showed band patterns that were similar to those from non-metastatic carcinomas and the sample from a case of cystic disease of the breast resembled the pattern for normal non-neoplastic breast tissue. This is the first instance of definitive diagnosis by this method. The piece of tissue was provided by the duty pathologist as being from a benign tumour, namely a fibroadenoma, on macroscopic appearance at initial inspection with the naked eye. It was then characterised as definitely non-neoplastic after PCR amplification of its cDNA, and subsequent microscopical examination of the tissue confirmed this.

To confirm that the differences seen with probe E4 are valid and not technical artifacts, the results obtained when the same filter was hybridised with probe P2 are shown in FIG. 2. This shows that i) all tissues examined expressed the standard form of the gene, ii) other exon splice products, not containing transcripts from exon 10/11, were present in tumours and metastases and iii) that the differences described above are not due to unequal loading of tracks in the various panels and lanes on this composite filter, but resulted from alternative splicing. All conditions in this experiment were the same as those in hybridisation with E4, except the exposure time of the filter to X-ray film (10 hours exposure for FIG. 1, versus 1.5 hours for FIG. 3).

EXAMPLE 2

Colon Samples

Figure 3:
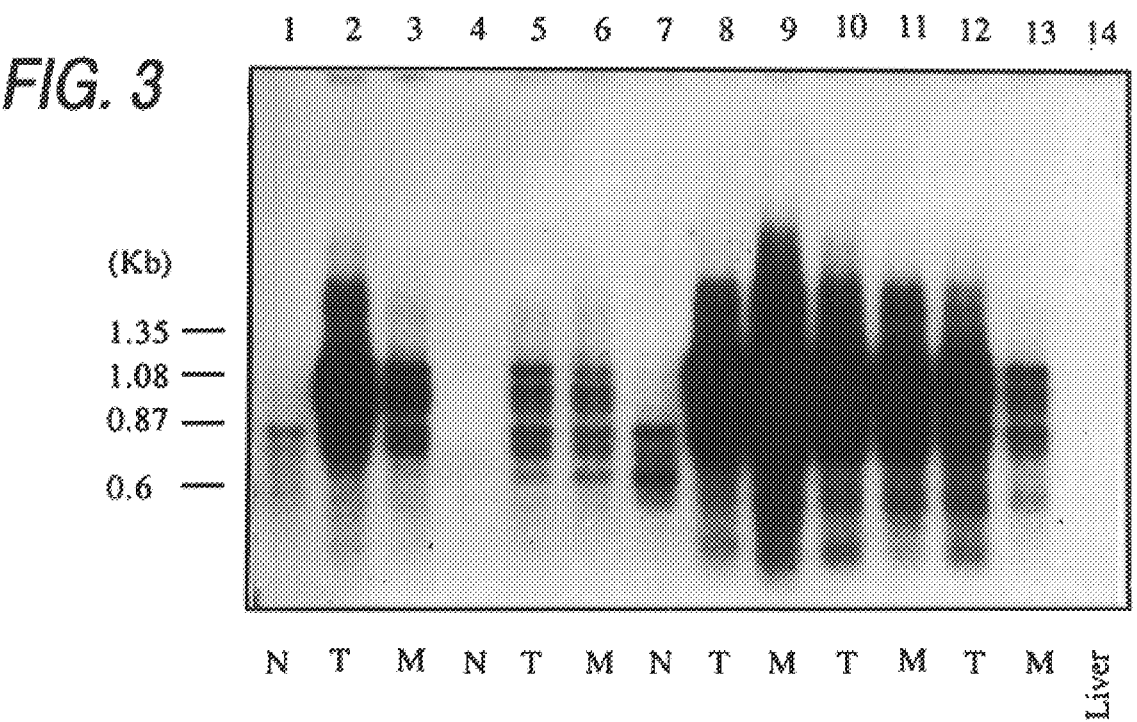
Figure 4:
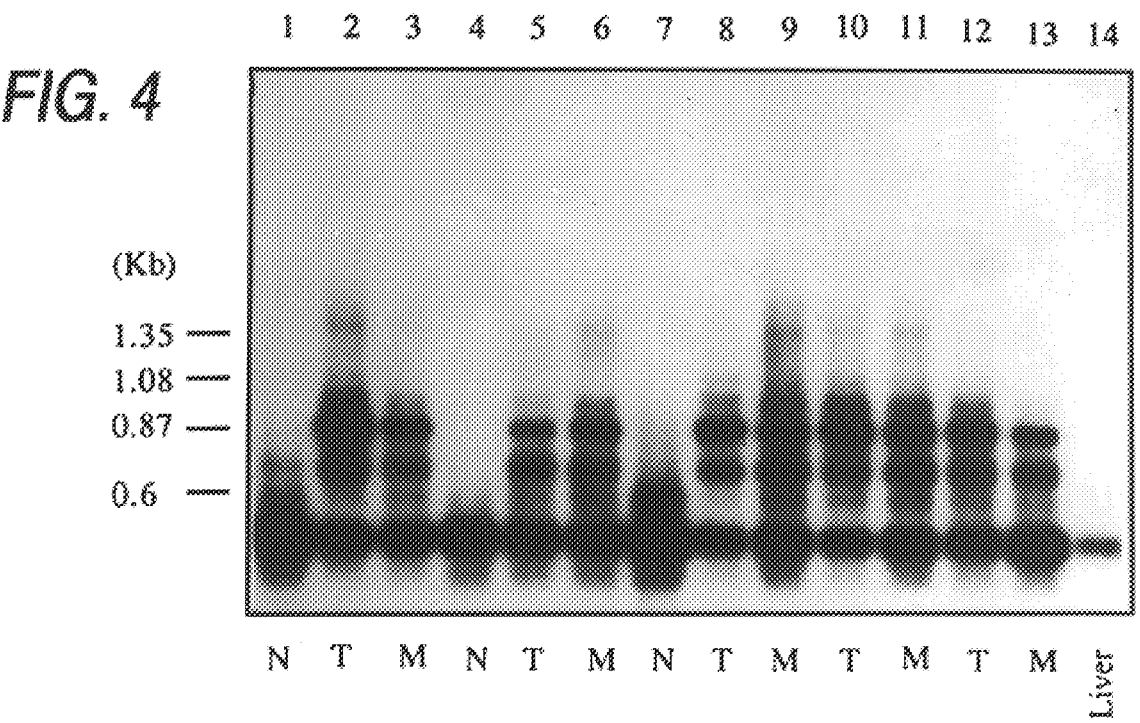
Figure 5A:
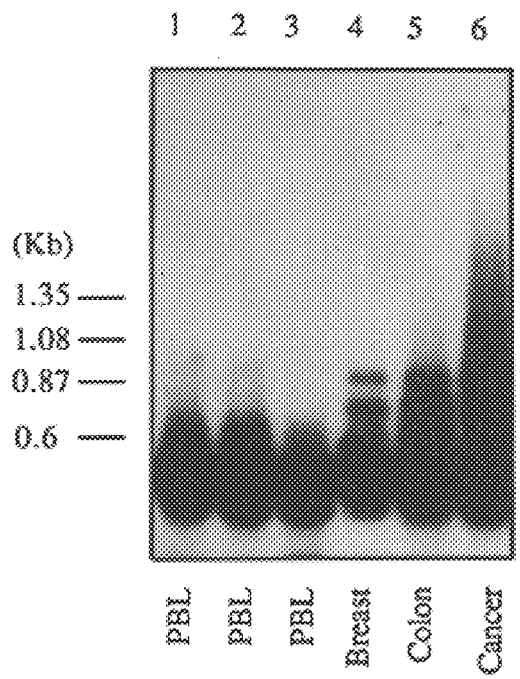
Figure 5B:
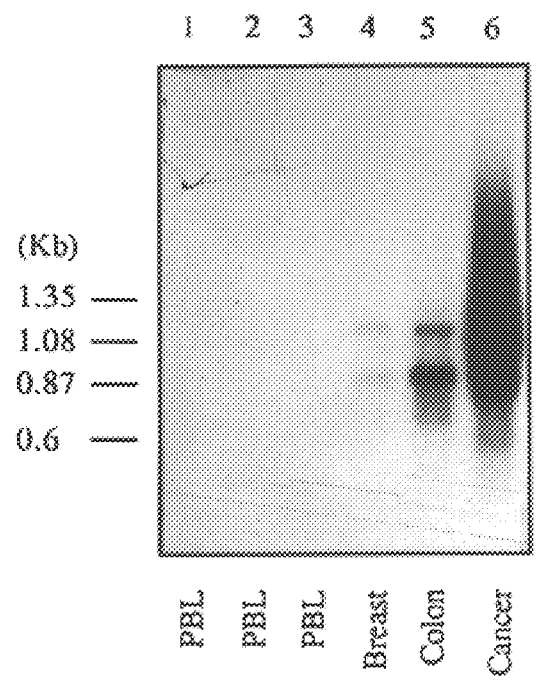

The findings in colon carcinoma were identical to those in breast carcinoma. Thus, in all cases the colon carcinoma tissues showed increased number of more intensely labelled, larger molecular weight bands with probe E4 (FIG. 3) than normal colonic mucosa and other normal tissues. As with breast carcinomas, hybridisation with probe P2 showed no differences in the degree of expression of the standard form of the molecule (FIG. 4).

EXAMPLE 3

Calibration of the Sensitivity of the Method

Examination of autoradiograms of PCR products of peripheral blood leukocytes seeded with known numbers of HT29 colon carcinoma cells showed the presence of additional bands characteristic of tumour cells, down to a level of 10 tumour cells in a sample of $10^7$ leukocytes. By fine-tuning the conditions of the assay it is considered possible to detect a single tumour cell in 10 ml of blood.

In the series described above, all samples of neoplastic tissue showed over-expression of alternatively spliced products of the CD44 gene and none of the samples from non-neoplastic tissue did so. Therefore, there was complete correspondence between normal or neoplastic origin of a sample and pattern of CD44 expression. In one instance, a tumour removed from a patient (patient B16, lane 14 in FIG. 1A) with no current clinical evidence of metastasis, was found to have a pattern of expression indicating metastatic capability. At present it is not possible to know whether this is a false positive result, or a sign of imminent metastasis. This patient is currently under observation in the follow-up clinic.

EXAMPLE 4

We have designed and synthesised oligonucleotide primers according to our current findings, as follows:

Primer P1=5'-GACACATATTGCTTCAATGCTTCAGC (458–484) (SEQ ID NO:3)

Primer P2=5'-CCTGAAGAAGATTGTACATCAGTCACAGAC (488–518) (SEQ ID NO:6)

Primer P3=5'-TGGATCACCGACAGCACAGAC (746–767) (SEQ ID NO:7)

Primer P4=5'-GATGCCAAGATGATCAGCCATTCTGGAAT (912–941) for standard part (Stamenkovic 1989) (SEQ ID NO:4)

Primer E1=5'-TTGATGAGCACTAGTGCTACAGCA (SEQ ID NO:8)

Primer E2=5'-CATTTGTGTTGTTGTGTGAAGATG (SEQ ID NO:9)

Primer E3-5"-AGCCCAGAGGACAGTTCCTGG (534–554) (SEQ ID NO:10)

Primer E4=5'-TGAGATTGGGTTGAAGAAATC (558–578) (SEQ ID NO:5)

Primer E5=5'-TCCTGCTTGATGACCTCGTCCCAT (585–608) (SEQ ID NO:11)

D1: 5'GAC AGA CAC CTC AGT TTT TCT GGA (63–86) (SEQ ID NO:12)

D5: 5'TTC CTT CGT GTG TGG GTA ATG AGA (888–911) (SEQ ID NO:13) for the exons (Hofmann 1991). E1 and E2 are on exon 6.

Fresh tissue samples 0.5–1 cm in diameter were obtained from surgical resection specimens or at autopsy. All samples used in this work were obtained from the residue of tissue remaining after diagnostic samples had been taken, and which would otherwise have been discarded. The samples were snap-frozen in liquid nitrogen within ten minutes of arrival at the pathological specimen reception area and kept frozen in nitrogen until use. cDNA was synthesised with viral reverse transcriptase using 5 μg of total cellular RNA as template, followed by PCR with Primer P1 and Primer P4. PCR amplification, electrophoresis and hybridisation were performed under standard conditions.

When the PCR products were hybridised with radiolabelled E2 or E4, all samples from carcinomas overexpressed several splice variants, but the pattern of bands seen with each probe was different. Hence, the oligonucleotide probe for Exon 6 products is very effective in distinguishing neoplastic from non-neoplastic samples, but not significantly more sensitive than E4, at least on samples from solid tissues, but is possibly useful for detecting organ of origin of a disseminating metastatic cell or an established metastasis. Subsequently, the same filters were stripped and hybridised with P2 probe to show that all samples, including normal tissues, produced the standard portion of CD44. This confirmed that the differences observed between the results obtained with normal and tumour samples, probed with E2 and E4, were not due to unequal loading of PCR products. The cumulative results are summarised in Table 1 which indicates that these changes are seen in a wide range of common cancers.

TABLE 1

| Type of Tissue | No. of Patients/ Volunteers | No. Showing Increased Splice Variants |
|---|---|---|
| Neoplastic | 47 | 46 |
| Breast Cancer | 21 | 21 |
| Colon Cancer | 13 | 13 |
| Bladder Cancer | 6 | 6 |

TABLE 1-continued

| Type of Tissue | No. of Patients/ Volunteers | No. Showing Increased Splice Variants |
|---|---|---|
| Stomach Cancer | 1 | 1 |
| Thyroid Cancer | 1 | 1 |
| Fibroadenoma | 2 | 2 |
| Prostate Cancer | 3 | 2 |
| Non-Neoplastic | 39 | 0 |
| Normal Breast | 9 | 0 |
| Cystic Disease of Breast | 1 | 0 |
| Normal Colon | 9 | 0 |
| Crohn's Disease | 1 | 0 |
| Ulcerative Colitis | 1 | 0 |
| Appendicitis | 1 | 0 |
| Normnal Bladder | 4 | 0 |
| PBL | 10 | 0 |
| Bone Marrow | 3 | 0 |

We have also examined some malignant tumours of bone muscle and observed a similar pattern, of marked overexpression of multiple spliced variants, in the osteosarcoma.

EXAMPLE 5

Cancer Diagnosis by PCR Assay of Clinically-Harvested Urine Samples

Approximately 50 ml naturally-voided urine were obtained from each person and transported to the laboratory as speedily as possible. Specimens from 90 patients were examined: 44 from patients with biopsy-proven bladder cancer, 46 from patients with non-neoplastic inflammation of the bladder (cystitis) and from normal volunteers. One ml of each urine sample was removed after thorough mixing and submitted for cytological examination. Another 1 ml of urine was checked by Fluorescein diacetate-ethidium bromide staining to assess the viability of cells in the sample. The remainder of the urine was centrifuged at 2000 rpm for 10 minutes and the cell pellet was kept at −70° C. until use. mRNA extraction was performed with oligo dT cellulose tablets (invitrogen). cDNA was synthesised with AMV reverse transcriptase (Invitrogen). The completed cDNA solution was divided equally into two tubes, one being for PCR with E1 and E5, to amplify the particular cDNA transcript, which we have found to be of diagnostic value and the other for PCR with P1 and P4 to amplify the standard form of CD44, with or without all splice variants, as an internal control.

Figure 8:
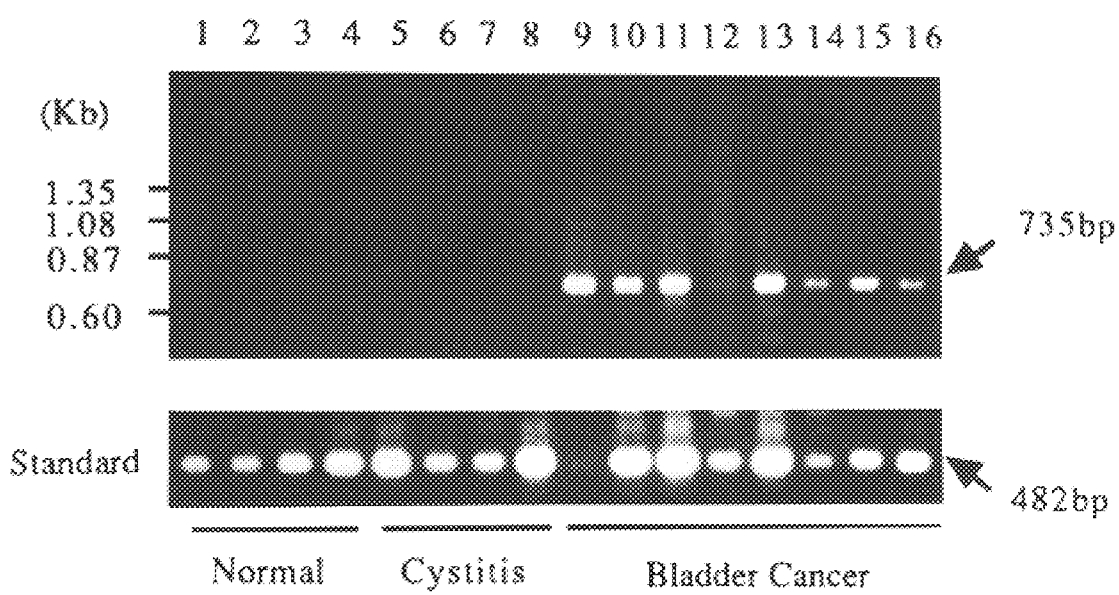
FIG. 8 is a set of autoradiographs showing the results of another experiment.

Thirty-five cycles PCR were then carried out. The cycle conditions were: 95° C. 1 minutes, 55° C. 1 minute, 72° C. 2 minutes. A hot start procedure was adopted for all samples. Results are shown in FIG. 8.

Equal volumes of PCR products were loaded in each lane of a 1.2% agarose gel and stained with ethidium bromide. If the cells in the urine were to be expressing all the Exons from Exon 6 to Exon 14, it was predicted that with the current PCR protocol, using primers E1 and E4, should produce a 735 bp band. There is no band in tracks containing cDNA from normal urine or that of patients with non-neoplastic cystitis (lanes 1–8) but a clear 735 band is seen in all urine samples from patients with bladder cancer (lanes 9–16) when PCR was performed with primer E1 and E5 (upper panel).

A 482 bp band representing the standard form of CD44 was obtained almost equally in all cases when PCR was performed with P1 and P4 (lower panels). This indicates that the diagnostically significant differences between urine from patients with bladder cancer and that from controls were not caused by unequal loading of the tracks but by alternative splicing of the CD44 gene. Lanes 1–4: normal urine. Lanes 5–8: cystitis urine. Lanes 9–16: from patients 1–8 with bladder cancer.

In the overall results this 735 bp band was completely absent in 7 of 7 normal and 9 of 9 cystitis-affected urine specimens; that is 0% false positive. Also 14 of 19 (74%) urine samples from patients with bladder cancer showed a positive result (i.e. 26% false negatives). In the false negative samples there was a shortage of viable cancer cells as indicated by fluorescein-d acetate ethidium bromide staining.

EXAMPLE 6

Stools from 12 patients were assayed by the techniques described herein. Of the samples from 9 patients with colorectal carcinoma, 5 gave positive results. Of the samples from 3 normal patients, all 3 gave negative results. These figures, obtained from samples full of bacteria which were not subjected to any pretreatment, encourage the belief that a viable diagnostic assay could be developed without difficulty.

In the inventors further experience of detecting tumour cells with this method, the following observations would be useful to others investigating its diagnostic potential. The major considerations to be aware of are that the reliability and reproducibility of the results depend critically on the quality of the mRNA obtained from the sample and upon the care with which the techniques are performed. The main requirement is to eliminate false negative results by ensuring that high quality mRNA is routinely obtained and by using internal standards in every reaction to monitor the PCR amplification step. False positives, providing they are not too frequent, are not a serious problem, because they can be recognised by replicate assays on the same or further samples and by reference to other clinical data.

The inventors have explored the procedures needed to ensure the routine RT-PCR detection of abnormal CD44 gene activity in small clinical samples containing tumour cells. If a tissue sample is divided into aliquots, half of which are frozen in liquid nitrogen immediately and the remainder of which are left at ambient temperature, one can show how the ability to detect CD44 splice variants declines with time and with mode of specimen handling. Fresh samples submitted to mRNA extraction within half an hour of excision give the most reliable results and there is a gradual decline in quality over the next few hours if the fresh tissue is left at ambient temperature. If the sample is first snap frozen, the results obtained when RNA is extracted immediately after thawing are satisfactory, but decline very rapidly, beginning within 15 minutes, the larger variant transcripts being lost first and ultimately even the standard form. It is also found that if snap-frozen cell and tissue samples are stored at −70° C. the results decline after 4 weeks, even if the mRNA is extracted immediately after thawing. It would seem therefore that degradation of RNA by ribonucleases released from cells ruptured during freezing continues, even at this temperature, although at slower rates. Further, as one would expect, if the sample taken for RNA extraction is from an area of necrosis or of fibrosis, one does not obtain the typical results seen with viable tumour tissue. Hence, care in sample selection and in specimen processing are both needed for generating reliable data.

Arising out of this, we prefer that a fresh sample should be held for not more than 24 hrs before being either frozen or treated to extract mRNA; and that a thawed sample should be held for not more than 2 hrs before being treated to extract mRNA.

The diagnosis method described herein can be performed in a single day, possibly in a few hours, and is capable of being automated. Use of the method has been demonstrated, on various tissue samples to detect a whole variety of cancers, and also on blood and urine samples. We therefore offer it as a convenient practical method for cancer screening and diagnosis. In principle it could also have wide general applicability to cancer detection and prevention programmes and therefore have epidemiologic and public health value. Proper application of its sensitivity, specificity and simplicity should add not only to initial cancer diagnosis but to evaluation of extent of disease in the body, to judgment of the efficacy of treatment and to early detection of tumour recurrences.

Figure Legends

Figure 1C:
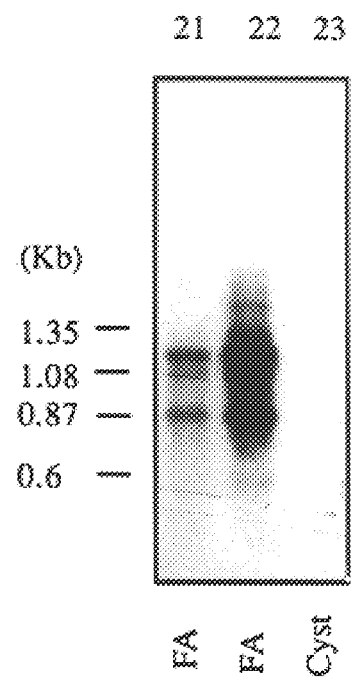

Notation: N=normal, T=primary tumour, M=metastasis.
FIGS. 1A–1C

Figure 2A:
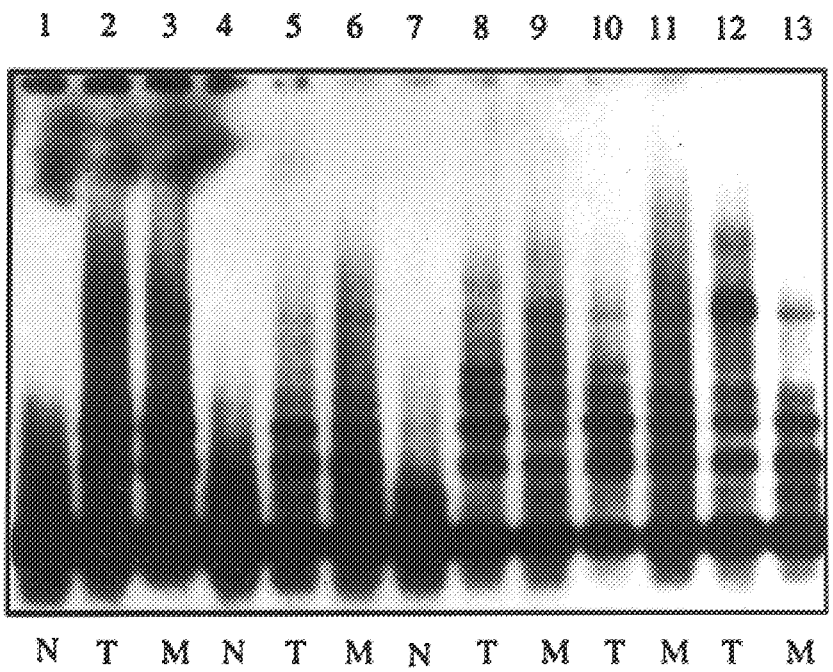
Figure 2B:
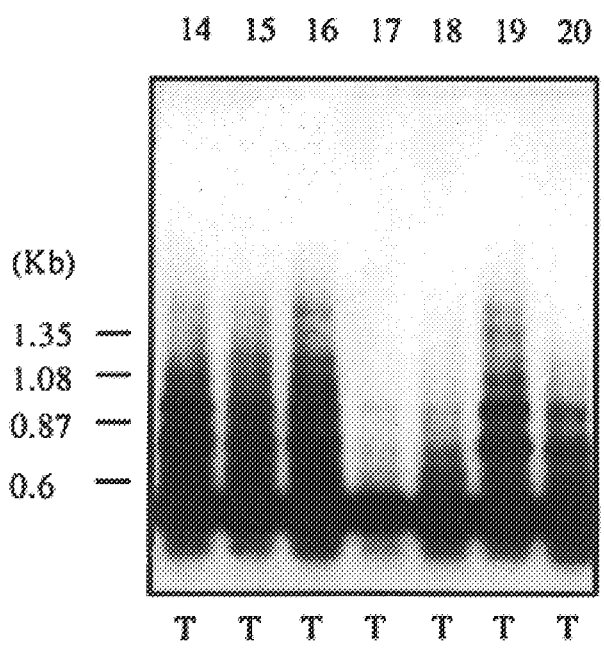
Figure 2C:
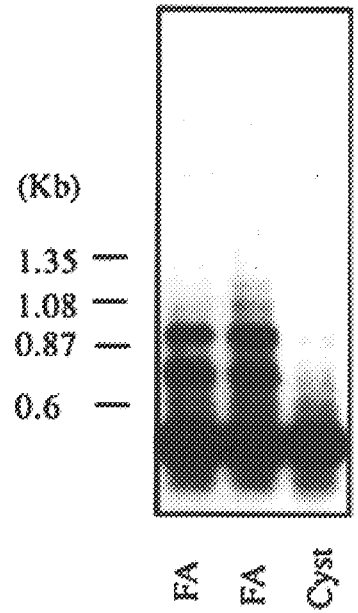

Autoradiogram of PCR products from breast tissue samples probed with E4 (10 hours exposure of X-ray film to sample filter). Panel A: malignant primary breast carcinomas with their metastases. Tracks 1, 2 and 3: patient B1; tracks 4, 5 and 6: patient B2; tracks 7, 8 and 9: patient B3; tracks 10 and 11: patient B4; tracks 12 and 13: patient B5. It can be seen that compared to normal breast tissue, primary breast carcinomas and their metastatic deposits overexpress several splice-variants. Note the doublet (arrows) at 1500 bp and 1650 bp best seen in track 5. This is present in all tumours and metastases but is fogged in the other tracks by this time of exposure. It is not detectable in any normal samples even at much longer exposure times (23 hours). Panel B: Breast carcinomas with no clinical evidence of metastasis. Tracks 14–20 are from patients B15–B21. The tumours all overexpress several variants, but show less bands and the signal intensity is less, except track 16 (patient B17)—see text. The 1500/1650 bp doublet (arrow) is easily recognisable in tracks 15, 16 and 18 at this length of exposure and became detectable in all other tumour-containing tracks on longer exposure. The illustration, however, shows only the shorter exposure, to avoid fogging the tracks which have stronger signals. Panel C: Fibroadenomas (FA) and fibrocystic disease of the breast (Cyst). Tracks 21 and 22, containing the benign tumour samples (samples B22 and 23), express more than the non-neoplastic sample (fibrocystic disease) in track 23 (sample B24).
FIGS. 2A–2C Autoradiogram of PCR products from breast tissue samples probed with probe P2 (1.5 hours exposure of X-ray film to sample filter). This result was obtained by reprobing the same filter as that used in FIG. 1, after stripping off the previous probe. Here it can be seen that i) the differences observed in FIG. 1 are not due to unequal loading of tracks, ii) that the expression of the standard form of the molecule is quantitatively greater than any of the variants, iii) the standard form is expressed in all tissues examined and iv) further variants which do not contain exon 3 transcripts, are also present and over-expressed in tumours. The 1500/1650 bp doublet can be recognised in the tumours in panel A but needed longer exposure to be detectable in panels B and C.
FIG. 3

Autoradiogram of PCR products from colon tissue samples probed with E4 (10 hours exposure of photographic film to sample filter). Tracks 1, 2 and 3: patient C1; tracks 4, 5 and 6: patient C2; tracks 7, 8 and 9: patient C3; tracks 10 and 11: patient C4; tracks 12 and 13: patient C5; track 14: normal liver sample. The picture shows the same features as described in the legend to FIG. 1 and that the findings apply to carcinomas of the colon. The 1500/1650 bp doublet (arrow) is easily recognisable in several tumour tracks (2 and 8–12) and the faint signal in the corresponding position in tracks 3, 5, 6 and 13 became stronger on longer exposure. However none appeared in this vicinity in tracks 1, 4, 7 or 14 (normal tissue).

FIG. 4

Autoradiogram of PCR products from colon tissue samples probed with P2 (1.5 hours exposure of photographic film to sample filter). This confirms equal loading of the tracks and that other points, illustrated in FIG. 2, apply to colon carcinomas. Note that normal liver expresses the standard form of CD44.

FIGS. 5A–5B

Autoradiogram of PCR products of normal peripheral blood leukocytes, PBL (from 3 different persons) and other normal tissues probed with E4 (panel A; 8 hours exposure to photographic film) and P2 (panel B; 5 hours exposure to photographic film). Track 6 contains PCR products from a breast cancer (patient B1) as a positive control. With this combination of primers and probes, leukocytes can be seen to express the standard form of the CD44 molecule, but no detectable splice variants. The samples in tracks 4 and 5 were from individuals with no clinical evidence of neoplasia, as follows: track 4, breast tissue obtained at autopsy from the body of a woman who died of bacterial endocarditis; track 5, colon resected for volvulus.

TABLE 2

| PATIENT | AGE | DISEASE | TUMOUR SIZE | METASTASIS | HISTOLOGY (GRADE) | CLINICAL STAGE |
|---------|-----|---------|-------------|------------|-------------------|----------------|
| B1 | 56 | Breast ca | 2.5 cm | Lymph node | | |
| B2 | 53 | Breast ca | 3 cm | Lymph node | | |
| B3 | 65 | Breast ca | 3 cm | Lymph node | | |
| B4 | 54 | Breast ca | 5 cm | Lymph node (10/10) | IDC (mucinous) [1] | |
| B5 | 59 | Breast ca | 5.5 cm | Lymph node | | |
| B6 | 59 | Breast ca | 3 cm | Lymph node | | |
| B7 | 61 | Breast ca | 4 cm | Lymph node (17/17) | ILC/IDC | 3 |
| B8 | 38 | Breast ca | 3.5 cm | Lymph node (1/5) | ILC | 2 |
| B9 | 65 | Breast ca | 1.8 cm | Lymph node (5/6) | ILC | 2 |
| B10 | 61 | Breast ca | | Lymph node (10/13) | IDC [1] | 2 |
| B11 | 80 | Breast ca | 11 cm | Lymph node | 3 | |
| B12 | 65 | Breast ca | 2.3 cm | Lymph node | ? 1 | |
| B13 | 68 | Breast ca | 2.8 cm | Lymph node (4/12) | IDC [3] | 2 |
| B14 | 47 | Breast ca | 7 cm | Lymph node | | 2 |
| B15 | 38 | Breast ca | | None (0/7) | IDC | 1 |
| B16 | 62 | Breast ca | 3 cm | None (0/4) | IDC [3] | 1 |
| B17 | 62 | Breast ca | 3 cm | None (0/16) | IDC [2] | 1 |
| B18 | 63 | Breast ca | 3 cm | None [0/6] | 1 | |
| B19 | 61 | Breast ca | 3 cm | None | 1 | |
| B20 | 42 | Breast ca | 4 cm | None | IDC | 1 |
| B21 | 65 | Breast ca | | Lymph node | IDC/ILC | |
| B22 | 54 | Breast ca | 6 cm | None (0/4) | IDC | 1 |
| B23 | 49 | Fibroadenoma | 4 cm | — | — | — |
| B24 | 47 | Fibroadenoma | 3 cm | — | — | — |
| B25 | 29 | Cystic disease | — | — | — | — |
| C1 | 72 | Colon ca | 5.0 cm | Lymph node | Well diff. adeno | 3 [C] |
| C2 | | Colon ca | | Lymph node | | |
| C3 | 65 | Colon ca | 6.5 cm | Liver | Mod diff. adeno | 4 [D] |
| C4 | 56 | Colon ca | 7.8 cm | Lymph node (and liver) | Mod diff. adeno | 4 [D] |
| C5 | | Colon ca | | Lymph node | | |
| C6 | 57 | Colon ca | 5 cm | Lymph node | Mod diff. adeno | 3 [C] |
| C7 | | Colon ca | | None | | |
| C8 | 75 | Colon ca | 6.5 cm | Lymph node | Mod diff. adeno | 3 [C] |
| C9 | 72 | Colon ca | 5.5 cm | Lymph node | Mod diff. adeno | 3 [C] |
| C10 | 76 | Colon ca | 4.5 cm | None | Well diff. adeno | 1 [B] |
| T1 | | Thyroid ca | | | | |

Key:
IDC: infiltrating ductal carcinoma
ILC: infiltrating lobular carcinoma
Well diff. adeno: Well differentiated adenocarcinoma
Mod diff. adeno: Moderately differentiated adenocarcinoma (SEQ ID NO: 13)
Letters in square brackets in Clinical Stage column refer to Dukes staging scheme for colon carcinoma

REFERENCES

1. Stamenkovic, Amiot M, Pesando J. M, Seed B. A lymphocyte molecule implicated in lymph node homing is a member of the cartilage link protein family. Cell 1989; 56: 1057–062.

2. Birch M, Mitchell S, Hart I. R. Isolation and characterisation of human melanoma cell variants expressing high and low levels of CD44. Cancer Res. 1991; 51: 6660–6667.

3. Gunthert U, Hofmann M, Rudy W, Reber S, Zoller M, HauBmann, Matzku S, Wenzel A, Ponta H, Herrlich P. A new variant of glycoprotein CD44 confers metastatic potential to rat carcinoma cells. Cell 1991; 65: 13–24.

4. Sy M S, Guo Y-J, Stamenkovic I. Distinct effects of two CD44 isoforms on tumor growth in vivo. J. Exp. Med 1991; 174: 859–866.

5. Hofmann M, Rudy W, Zoller M, Tolg C, Ponta H, Herrlich P, Gunthert U. CD44 splice variants confer metastatic behaviour in rats: Homologous sequences are expressed in human tumor cell lines. Cancer Res. 1991; 51: 5292–5297.

6. Stamenkovic I, Aruffo A, Amiot M, Seed B. The hematopoietic and epithelial forms of CD44 are distinct polypeptides with different adhesion potentials for hyaluronate-bearing cells. EMBO J. 1991; 10: 343–348.

7. Jackson D. G, Buckley J, Bell J. I. Multiple variants of the human lymphocyte homing receptor CD44 generated by insertions at a single site in the extracellular domain. J. Biol. Chem. 1992; 267: 4732–4739.

8. Chomzynski P, Sacchi N. Single-step method of RNA isolation by acid guanidinium thiocyantat-phenol-chloroform extraction. Anal Biochem. 1987; 162: 156.

9. Knudson A. G. Hereditary cancer, oncogenes and antioncogenes. Cancer Res. 1985; 45: 1437–43.

10. Tarin D. Tumour metastasis. In: Oxford Textbook of Pathology 1992; (eds: J O'DMcGee, N. A. Wright, P. G. Isaacson). Oxford University Press, Oxford. pp 607–633.

11. Hayle A. J, Darling D. L, Taylor A. R, Tarin D. Transfection of metastatic capability with total genomic DNA from metastatic tumour cell lines. Differentiation, 1993, in press.

12. Screaton G. R., Bell M. V., Jackson D. G., Cornelis F. B., Gerth U., and Bell J. I., Genomic Structure of DNA encoding the lymphocyte homing receptor CD44 reveals at least 12 alternatively spliced exons, Proc. Natl. Acad. Sci. USA, Vol 889, p 12160–4, December 1992, Immunology.

We claim:

1. A method of diagnosis of neoplasia, which method comprises analyzing CD44 gene expression in a sample by the steps of making complimentary DNA (cDNA) from messenger RNA (mRNA) in the sample, amplifying portions of the cDNA corresponding to the CD44 gene, and detecting the amplified cDNA thereby diagnosing neoplasia.

2. The method as claimed in claim 1 wherein the sample is from a tissue which may be a solid tumour or from blood or other body fluid.

3. The method as claimed in claim 1 wherein the sample is non-invasively obtained.

4. A method as claimed in claim 1 wherein a labelled specific oligonucleotide primer or probe is used in detection of the cDNA.

5. The method as claimed in claim 1 wherein the amplification is carried out via polymerase chain reaction.

6. The method as claimed in any one of claim 1 wherein the amplified cDNA is size separated by electrophoresis prior to detection.

7. The method as claimed in claim 6, wherein blotting and autoradiography are performed on the separated cDNA.

8. In pure form, the exon of CD44 having the nucleic acid sequence shown in FIG. 7 (SEQ ID NO:1), and a polynucleotide that is fully complementary thereto.

9. An oligonucleotide selected from the group consisting of 5'-TTGATGAGCACTAGTGCTACAGCA (SEQ ID NO:8) and 5'-CATTTGTGTTGTTGTGTGAAGATG (SEQ ID NO:9).

* * * * *

SEQUENCE LISTING ( 1 ) GENERAL INFORMATION:

( i i i ) NUMBER OF SEQUENCES: 13

( 2 ) INFORMATION FOR SEQ ID NO: 1:

( i ) SEQUENCE CHARACTERISTICS:
        ( A ) LENGTH: 141 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: CDS
        ( B ) LOCATION: 7..135

( x i ) SEQUENCE DESCRIPTION: SEQ ID NO: 1:

```
GCTACC ACT TTG ATG AGC ACT AGT GCT ACA GCA ACT GAG ACA GCA ACC         48
       Thr Leu Met Ser Thr Ser Ala Thr Ala Thr Glu Thr Ala Thr
        1               5                      10

AAG AGG CAA GAA ACC TGG GAT TGG TTT TCA TGG TTG TTT CTA CCA TCA         96
Lys Arg Gln Glu Thr Trp Asp Trp Phe Ser Trp Leu Phe Leu Pro Ser
15                  20                  25                  30

GAG TCA AAG AAT CAT CTT CAC ACA ACA ACA CAA ATG GCT GGTACG            141
Glu Ser Lys Asn His Leu His Thr Thr Thr Gln Met Ala
                 35                  40
```

( 2 ) INFORMATION FOR SEQ ID NO: 2:

( i ) SEQUENCE CHARACTERISTICS:
        ( A ) LENGTH: 43 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Thr Leu Met Ser Thr Ser Ala Thr Ala Thr Glu Thr Ala Thr Lys Arg
 1               5                  10                  15

Gln Glu Thr Trp Asp Trp Phe Ser Trp Leu Phe Leu Pro Ser Glu Ser
            20                  25                  30

Lys Asn His Leu His Thr Thr Thr Gln Met Ala
             35                  40
```

( 2 ) INFORMATION FOR SEQ ID NO: 3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear (  i i  ) MOLECULE TYPE: DNA (genomic)

(  x i  ) SEQUENCE DESCRIPTION: SEQ ID NO: 3:

GACACATATT GCTTCAATGC TTCAGC 26

( 2 ) INFORMATION FOR SEQ ID NO: 4:

(  i  ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear (  i i  ) MOLECULE TYPE: DNA (genomic)

(  x i  ) SEQUENCE DESCRIPTION: SEQ ID NO: 4:

GATGCCAAGA TGATCAGCCA TTCTGGAAT 29

( 2 ) INFORMATION FOR SEQ ID NO: 5:

(  i  ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (  i i  ) MOLECULE TYPE: DNA (genomic)

(  x i  ) SEQUENCE DESCRIPTION: SEQ ID NO: 5:

TGAGATTGGG TTGAAGAAAT C 21

( 2 ) INFORMATION FOR SEQ ID NO: 6:

(  i  ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear (  i i  ) MOLECULE TYPE: DNA (genomic)

(  x i  ) SEQUENCE DESCRIPTION: SEQ ID NO: 6:

CCTGAAGAAG ATTGTACATC AGTCACAGAC 30

( 2 ) INFORMATION FOR SEQ ID NO: 7:

(  i  ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (  i i  ) MOLECULE TYPE: DNA (genomic)

(  x i  ) SEQUENCE DESCRIPTION: SEQ ID NO: 7:

TGGATCACCG ACAGCACAGA C 21

( 2 ) INFORMATION FOR SEQ ID NO: 8:

(  i  ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear (  i i  ) MOLECULE TYPE: DNA (genomic)

(  x i  ) SEQUENCE DESCRIPTION: SEQ ID NO: 8:

```
TTGATGAGCA CTAGTGCTAC AGCA                                                              24
```

( 2 ) INFORMATION FOR SEQ ID NO: 9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 9:

```
CATTTGTGTT GTTGTGTGAA GATG                                                              24
```

( 2 ) INFORMATION FOR SEQ ID NO: 10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 10:

```
AGCCCAGAGG ACAGTTCCTG G                                                                 21
```

( 2 ) INFORMATION FOR SEQ ID NO: 11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 11:

```
TCCTGCTTGA TGACCTCGTC CCAT                                                              24
```

( 2 ) INFORMATION FOR SEQ ID NO: 12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 12:

```
GACAGACACC TCAGTTTTTC TGGA                                                              24
```

( 2 ) INFORMATION FOR SEQ ID NO: 13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 13:

```
TTCCTTCGTG TGTGGGTAAT GAGA                                                              24
```